United States Patent [19]
Klose et al.

[11] Patent Number: 4,985,204
[45] Date of Patent: Jan. 15, 1991

[54] DEVICE FOR CARRYING OUT A HETEROGENEOUS REACTION

[75] Inventors: Sigmar Klose, Berg; Klaus Erler, Pöcking; Wolfgang Uhl, Weilheim; Manfred Baier, Seeshaupt, all of Fed. Rep. of Germany

[73] Assignee: Boehringer Mannheim GmbH, Mannheim-Waldhof, Fed. Rep. of Germany

[21] Appl. No.: 159,253

[22] Filed: Feb. 23, 1988

[30] Foreign Application Priority Data

Mar. 2, 1987 [DE] Fed. Rep. of Germany ....... 3706718

[51] Int. Cl.⁵ ...................... G01N 31/22; G01N 21/03
[52] U.S. Cl. ........................................ 422/56; 422/58; 422/69; 422/103; 436/165; 436/169
[58] Field of Search ....................... 422/58, 61, 69, 72, 422/101, 55, 56, 57, 103; 436/165, 169, 170, 808, 824, 825, 807, 809, 810; 435/7, 30, 288, 299–301, 810

[56] References Cited

U.S. PATENT DOCUMENTS

| 3,799,742 | 3/1974 | Coleman | 422/61 |
| 4,260,687 | 4/1981 | Jacobson et al. | 422/61 |
| 4,425,438 | 1/1984 | Bauman et al. | 436/810 |
| 4,426,451 | 1/1984 | Columbus | 436/165 |
| 4,515,889 | 5/1985 | Klose et al. | 422/101 |
| 4,690,899 | 9/1987 | Klose et al. | 422/72 |
| 4,732,848 | 3/1988 | Lenz et al. | |
| 4,756,884 | 7/1988 | Hillman et al. | 422/73 |

FOREIGN PATENT DOCUMENTS

| 0049898 | 4/1984 | European Pat. Off. |
| 0230618 | 8/1987 | European Pat. Off. |
| 3430905 | 2/1986 | Fed. Rep. of Germany |

Primary Examiner—Robert A. Wax
Assistant Examiner—William H. Beisner
Attorney, Agent, or Firm—Felfe & Lynch

[57] ABSTRACT

The present invention provides a device for carrying out a heterogeneous reaction for the determination of a component of a sample liquid on a first capillary action carrier present in a measurement chamber, to which carrier adheres at least one non-soluble reagent, wherein at least one soluble reagent is present on a second capillary action carrier in a first pre-chamber, which carrier is in capillary contact with the capillary action carrier in the measurement chamber, which first pre-chamber is connected via a first capillary with a first application chamber to be filled from outside through a filling opening and the measurement chamber is also connected with a waste chamber by a capillary arrangement through which can only flow a liquid under a predetermined gravitational force into the measurement chamber.

49 Claims, 4 Drawing Sheets

DEVICE FOR CARRYING OUT A HETEROGENEOUS REACTION

The present invention is concerned with a device for carrying out a heterogeneous reaction for the determination of a component of a sample liquid on a first capillary-active carrier present in a measurement chamber, to which carrier adheres at least one nonsoluble reagent.

It is an object of the present invention to provide a device of this kind by means of which, solely with the use of gravitational force—at most with rotation of the device into different positions—a heterogeneous reaction can be dependably carried out for the detection of a component of a sample liquid (analyte).

Heterogeneous reactions for the detection of analytes, i.e. reactions between an analyte and at least one soluble and at least one insoluble reagent, in which case one or more reactions take place, can generally not be carried out in one step. Depending upon the type of reaction, excess sample material or reagent must be removed (washing step), adjuvant reagents added thereto and/or, after completion of a reaction (incubation step), a further reagent, for example an indicator reagent, must be added thereto.

These steps usually involve operations such as pipetting, dosing and homogenisation which can only be dependably carried out by trained personnel. With the device according to the present invention, such operations in the case of analyses are to be avoided and, therefore, analyses with the use of heterogeneous reactions are also to be capable of being carried out simply and with sufficient exactitude also be untrained users. Even in the case of not quite expert handling, the analyses are to take place from one apparatus to another in the same way and thus give the same measurement results, the measurement results thereby being indicated optically or being determinable in another manner to be explained hereinafter.

A device according to the present invention is also to be capable of construction especially as disposable device for carrying out tests (especially a pregnancy test). They are to be capable of production as mass articles and not to require any individual operations.

SUMMARY OF THE INVENTION

Thus, according to the present invention, there is provided a device for carrying out a heterogeneous reaction for the determination of a component of a sample liquid on a first capillary-action carrier present in a measurement chamber, to which carrier adheres at least one non-soluble reagent. At least one soluble reagent is present on a second capillary-action carrier in a first pre-chamber, which carrier is in capillary contact with the capillary-action carrier in the measurement chamber. The first chamber is connected via a first capillary with a first application chamber to be filled from outside through a filling opening The measurement chamber is also connected with a waste chamber by a capillary arrangement through which a liquid can only flow under a predetermined gravitational force into the measurement chamber.

The reaction components in the meaning of the present invention are the analyte, at least one soluble reagent and at least one insoluble reagent. Such reagents are well known and do not require a detailed explanation.

The device is especially useful for carrying out enzymatic and/or immunological determinations, especially with the use of enzymes, substrates, antibodies, antigens, haptens, colour-forming reagents and adjuvant reagents, such as buffers or tensides, for example for dissolving off the analytes from serum components.

In an especially preferred embodiment, the device is used for carrying out immunological determination processes, such as competitive, sandwich and DASP-sandwich tests. Such processes are described, for example, in laboratory techniques in Biochem. and Molec. Biol., ed. R. H. Burdon and P. H. v. Knippenberg, pub. Elsevier, Amsterdam, Vol. 15, pp. 9–37/1985 and Lig. Rev., 3/3, 6–13/1981. In the case of such processes of determination, the analyte is bound directly or indirectly to the insoluble reagent. Simultaneously or in further steps, via a detection reaction, for example a colour formation, there can be determined how much analyte has been bound.

DETAILED DESCRIPTION OF THE PREFERRED EMBODIMENTS

Characteristic features which the devices have in common are only described once.

Figure 1:
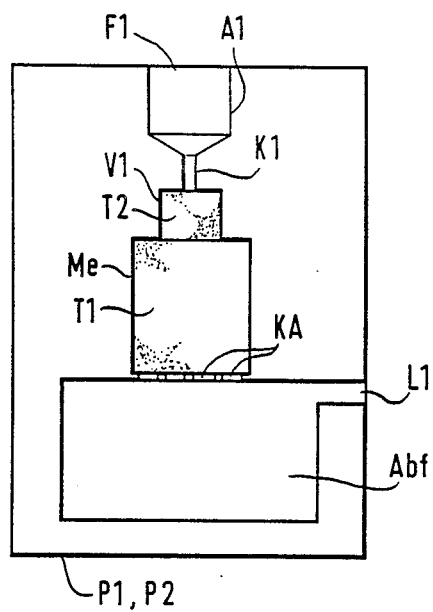
FIG. 1 is a schematic view of a first embodiment of the device.
Figure 2:
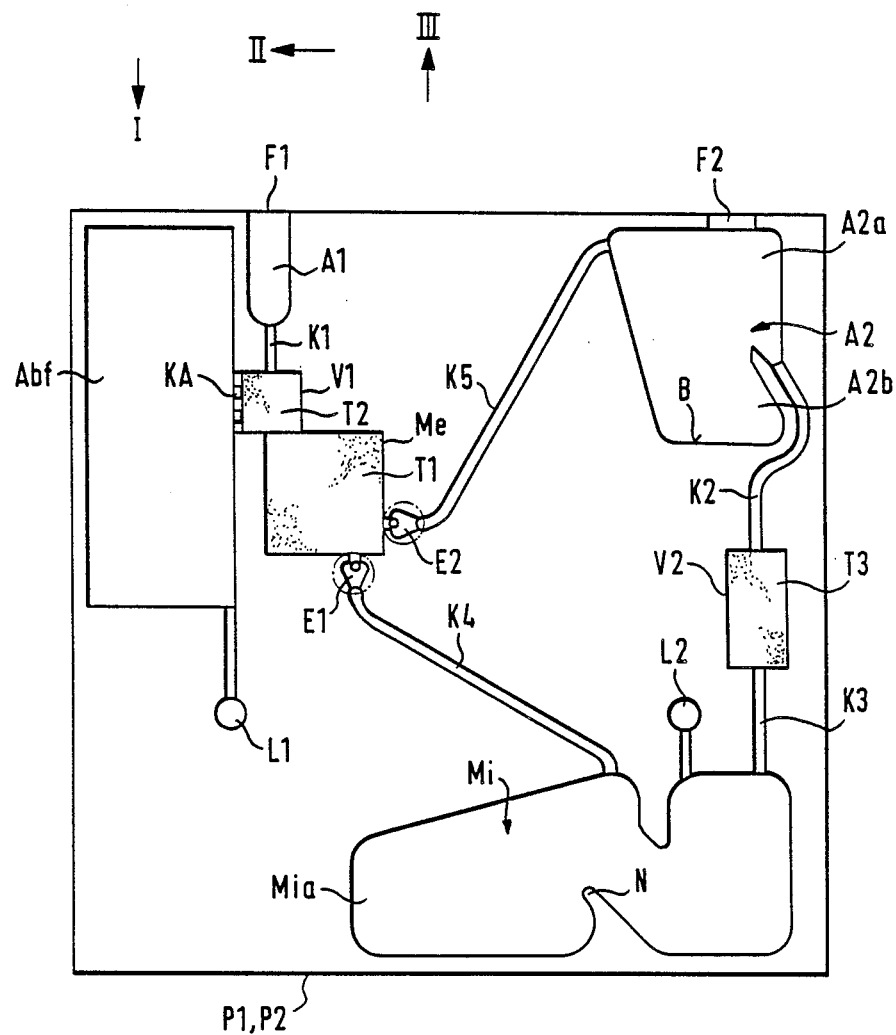
FIG. 2 is a schematic view of a second embodiment of the device.
Figure 3:
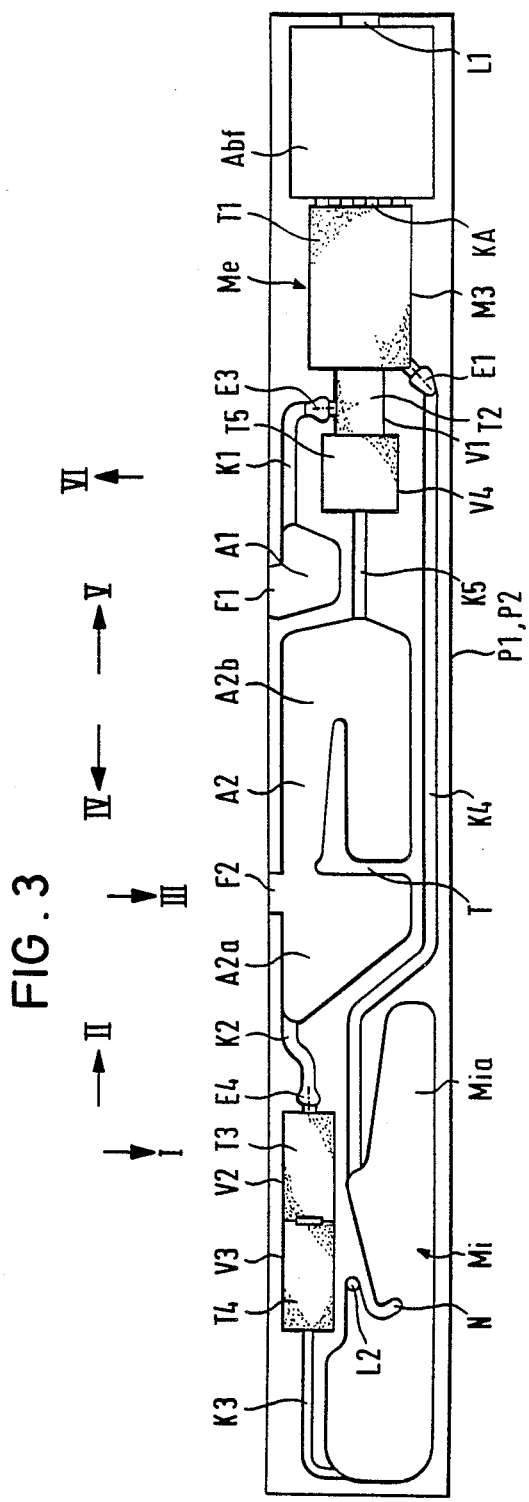
FIG. 3 is a schematic view of a third embodiment of the device.

The device according to FIGS. 1 to 3 serve for carrying out a heterogeneous reaction for the determination of a component of a sample liquid (analyte) on a first capillary action carrier T1 present in a measurement chamber, on which carrier adheres a non-soluble reagent. At least one soluble reagent is present on a second capillary action carrier T2 standing in capillary contact with the capillary action carrier T1 in measurement chamber Me, the second carrier being in a first pre-chamber V1. "Capillary contact" means that the capillary action carriers T1 and T2 are in capillary contact in such a manner that the capillary-active carrier T1 can take up in its capillaries liquid from the capillaries of the capillary-active carrier T2. The pre-chamber V1 is connected via a first capillary K1 with a first application chamber A1 to be filled from outside through a filling opening F1, this application chamber being the only one in the embodiment according to FIG. 1. The measurement chamber is also connected by a capillary arrangement KA, through which can only flow a liquid standing under a predetermined gravitational force away from the direction of the measurement chamber Me, with a waste chamber Abf, the capillary arrangement KA thereby forming an inlet of the waste chamber Abf. The waste chamber Abf is provided with a ventilation opening L1.

The capillary K1 has (which also applies to the capillaries described hereinafter) a hydraulic diameter of 0.05 mm. to 2 mm. and preferably a hydraulic diameter of 0.2 mm. to 0.6 mm. (The hydraulic diameter is defined as being four times the quotient of the cross-sectional surface and circumference of the capillary, whereby capillaries of non-circular cross-section can also be used.

As capillary-active carriers T1 and T2, there can be used, for example, paper, fleece, fabrics, woven materials or porous membrane materials, which also applies to the capillary action carriers described hereinafter.

The capillary action carriers can be characterised by their absorbent capacity and by their absorbent power. As measure for their absorbent power, there can be used the absorbent height or capillary rise with which they draw up a liquid in a predetermined time (300 s), the absorbent height thereby being the height of the front of the absorbed liquid over the level of the free liquid into which the capillary action carrier is dipped. Furthermore, the initial speed of absorption can be of importance, for example the time for the achievement of a absorbent height of 30 mm. In individual cases, the air permeability can also be of importance. Capillary action carriers with the following properties are especially preferred:

|  | range | preferred |
|---|---|---|
| suction capacity | 400–1200 ml/m$^2$ | 700–1100 ml/m$^2$ |
| suction height (in 300 s.) | 40–150 mm | 80–120 mm |
| initial speed of the absorption | 4–40 s/30 mm | 4–10 s/30 mm |
| air permeability | 4–5 l/min m$^2$ |  |

Such capillary action carriers are described, for example, in Federal Republic of Germany patent Specification No. 35 43 749 but the periodate activation there mentioned is not necessary for the carriers which can here be used.

The chambers A1, V1, Me and Abf, the capillaries K1 and the capillary arrangement KA are (which also applies to the chambers, capillaries, capillary arrangements and capillary flow-one-way valves described hereinafter) incorporated in a flat surface of a first plate P1 which is covered by a plane surface of a second plate P2. At least one of the plates P1 and P2 is thereby transparent at least in the region of the measurement chamber Me in order that the necessary measurement or observation of the heterogeneous reaction can be carried out.

As materials for the plates P1 and P2, glass or synthetic resin are especially appropriate, preferred synthetic resins including polyacrylate and polystyrene.

When using the device according to FIG. 1, on the carrier T2 is present a soluble reagent and on the carrier T1 an insoluble reagent. For carrying out a heterogeneous reaction, a predetermined amount of a sample liquid is first introduced into the application chamber A1. This liquid dissolves reagent from the carrier T2 and flows with this to carrier T1. Then, possibly after an incubation period, a predetermined amount of a diluent (a wash or elution solution) is introduced into the application chamber A1 which substantially frees the carrier T2 from reagent and transfers the reagent to carrier T1, excess liquid thereby passing through the capillary arrangement KA into the waste chamber Abf.

The waste chamber contains either uncovered fleece or fleece which is impregnated with reagents which there suppress still continuing and undesired detection reactions, such as colour formation or luminescence.

The capillary K1 ensures that a uniform, gradual distribution of the liquid in question, which flows to it through the application chamber A1, takes place on the carrier T2.

The capillary arrangement KA is essentially a one-dimensional lattice which, on the basis of the surface tension of the liquid passing from above to the lattice openings, first does not allow the liquid through but only when the liquid acts upon the latticework with a predetermined pressure brought about by the gravitational force. The capillary arrangement KA results in the carrier T1 filling with a predetermined amount of the reaction product or mixture of analyte and soluble reagent.

Subsequently, a predetermined amount of a further reagent is introduced into the application chamber A1 which reacts with the reagents present on the carrier T1.

The reaction can be observed, for example, by coloration of the carrier T1. However, it can also take place by measurement by means of reflectometry or by measurement of fluorescence or luminescence when a reagent or the diluent contains a fluorogenic or luminogenic component.

In the case of the embodiments according to FIGS. 2 and 3, a second application chamber A2, to be filled from the outside through a filling opening F2, is connected via a second capillary K2 with a second pre-chamber V2 in which is present at least one further reagent on a third capillary action carrier T3. Via a third capillary K3, the second pre-chamber V2 is connected with an empty mixing chamber Mi which, in turn, is connected via a fourth capillary K4 with the measurement chamber Me.

Into the mixing chamber Mi projects a nose N over which liquid entering from the third capillary K3 into the mixing chamber Mi flows upon tipping the mixing chamber Mi into a part Mia of the mixing chamber Mi, from which part Mia the liquid is conducted away by the fourth capillary K4. The second application chamber A2 is, in addition, connected via a fifth capillary K5 with the measurement chamber Me.

In the case of the embodiment according to FIG. 2, the second capillary K2 goes from the region of the second application chamber A2 which lies in about the middle between its filling opening F2 and its bottom B lying opposite the filling opening F2 so that the application chamber A2, in the position of the device illustrated in FIG. 2, is divided into an upper region A2a and a lower region A2b. The fifth capillary K5 goes from a position in the upper region A2a of the second application chamber A2 which lies at about the height of the filling opening F2.

The capillaries K4 and K5, which lead to the measurement chamber Me containing the capillary carrier T1, are connected with the measurement chamber Me via static capillary flow one-way valves E1 and E2, respectively, through which flow can only take place in the direction of the measurement chamber Me in order to ensure that the capillaries K4 and K5 do not again absorb liquid which has passed through them to the carrier T1. It is especially important that liquid which passes through the capillary K4 to the carrier T1 in the measurement chamber Me is not absorbed by the capillary K5 and that liquid which passes through the capillary K5 to the carrier T1 in the measurement chamber Me is not sucked up by the capillary K4.

In the case of this embodiment, the mixing chamber Mi is also provided with a ventilation opening L2.

When using the embodiment according to FIG. 2, in the position illustrated in FIG. 2 (arrow I points downwardly), the application chamber A1 is filled with sample liquid and the application chamber A2 with diluent. The application chamber A1 empties through the capillary K1 via the carrier T2, on which is present the soluble reagent, into carrier T1.

The diluent in the upper region A2a of the application chamber A2 elutes the carrier T3, on which is present a further soluble reagent, into the mixing chamber Mi. The diluent first remaining in the lower region A2b of the application chamber A2 is later emptied via the capillary K5 into the carrier T1. In the case of this embodiment, the washing out of carriers T1 and T2 takes place with the diluent which flows over the capillaries K4 and K5 and takes with it reagent not fixed on the carrier T1 in counterflow to the direction of flow of the sample liquid.

The diluent, which passes with the soluble reagent from T3 or through the capillary K3 into the mixing chamber Mi, flows, upon tilting the device into the position in which the arrow II points downwardly, over the nose N into the region Mia, the diluent thereby being homogenised with the indicator reagent.

The following Examples are given for the purpose of illustrating the present invention:

EXAMPLE 1

This Example describes a heterogeneous immunoassay for LH (human luteinising hormone) according to the DASP principle. This principle and the preparation of the reagents, for example of the monoclonal antibodies and conjugates, is described, for example, in European patent Specification No. 0,098,590 and the literature mentioned therein of the prior art.

Initial state:

As fleece there are used:

fleece A: 40% linters, 60% polyamide
fleece B: 40% polyamide, 30% viscose, 20% linters
fleece C: 80% polyester, 20% sulphite cellulose.

In the waste chamber Abf were present uncoated fleece A (10 mm.×25 mm., 0.8 mm. thick).

In the pre-chamber V1 is present a fleece B (4 mm.×4 mm., 0.5 mm. thick), impregnated with the soluble reagents: 100 mM HEPES (pH 7.2), 1% bovine serum albumin (BSA), 0.9% sodium chloride, 30 mU/test of a conjugate of monoclonal antibodies (mouse, MAK1 NCACC 84 122 005) against LH and β-galactosidase and 250 ng./test monoclonal antibodies (mouse) against LH, directed against another epitope (MAK2 NCACC 84 122 001).

The monoclonal antibodies MAK1 and MAK2 have been deposited under the above-given deposition numbers with the European Collection of Animal Cell Cultures in Great Britain.

In measurement chamber Me is present a fleece C (8 mm.×8 mm., 0.6 mm. thick) impregnated with 1% BSA, 39 μg./test polyclonal antibodies (sheep) directed against the Fcγ part of mouse IgG (insoluble reagent).

In the second pre-chamber V2 is present a fleece B (84 mm.×8 mm., 0.5 mm. thick) impregnated with an indicator reagent containing 70 mM HEPES (pH 7.2), 2 mM magnesium L-aspartate, 2 mM boric acid, 0.3% (w/v) BSA, 4.0 mM chlorophenol red β-galactoside (see European patent Specification No. 0,146,866) and 0.15% Tween 20.

The loading of the fleece (impregnation) takes place as described in Federal Republic of Germany patent Specification No. 35 43 749 but without periodate activation.

1st step

In the position illustrated in FIG. 2 (arrow I pointing downwardly), 15 μl. of LH-containing serum are introduced into the application chamber A1. The serum elutes the fleece T2 and passes to fleece T1.

2nd step

The application chamber A2 is filled with 450 μl. 0.9% sodium chloride solution. The part of this solution present in the upper region A2a of the application chamber A2 flows through the capillary K2, the fleece T3 and the capillary K3 downwardly into the mixing chamber Mi.

3rd step

After 10 minutes, incubation on fleece T1 is finished and the device is turned in such a manner that the arrow II points downwardly. In this way, the liquid which has passed from the capillary K3 into the mixing chamber Mi flows over the nose N into the region Mia of the mixing chamber Mi, which results in a homogenisation of the liquid.

The diluent from the lower region A2b of the application chamber A2 flows through the capillary K5 via the one-way valve E2 into the measurement chamber Me and subsequently into the pre-chamber V1, whereby it washed out the fleece T1 and T2. Subsequently, the liquid passes through the capillary arrangement KA into the waste chamber Abf.

4th step

The device is turned in such a manner that the arrow III points downwardly. The diluent with the indicator reagent thereby flows from the mixing chamber Mi via the capillary K4 and the one-way valve E1 into the measurement chamber Me so that the detection reaction is brought about on the fleece T1.

5th step

The detection reaction is observed or measured on the fleece T1 in the above-described way.

In the case of the embodiment of the device according to FIG. 3, the second pre-chamber V2 lies in series with a third pre-chamber V3 in which is present an adjuvant reagent with a fourth capillary-active carrier T4 (fleece B, 6 mm.×6 mm., 0.5 mm. thick), impregnated with 0.15% Tween 20 (w/v). Furthermore, the second application chamber A2 is connected via a fourth pre-chamber V4, in which is present a capillary-active carrier T5, with the first pre-chamber V1. The second application chamber A2 is divided by a separating wall T into two regions A2a and A2b. The region A2a is connected via the second capillary K2 and a one-way valve E4 with the second pre-chamber V2 and, furthermore, in this region A2a is the filling opening F2. The other region A2b is connected via the fifth capillary K5 with the fourth pre-chamber V4.

The application chamber A1 serves for the reception of the sample liquid and the application chamber A2 for the reception of the diluent. The diluent is distributed into the regions A2a and A2b.

Adjuvant and indicator reactions, as well as detection reactions, take place on carriers T5, T2 and T1.

The diluent flows from the application chamber A2 through the pre-chambers V2 and V3 into the mixing chamber Mi. (The nose N in FIG. 3 is only provided as a protection against running off of liquid via the ventilation hole L2 and does not serve for the homogenisation). The capillary K4, which leads from the mixing chamber Mi to the measurement chamber Me, can possibly be interrupted by at least one further pre-chamber in which is present a capillary action carrier, for example for controlling the rate of flow and for admixing inhibitors into the flow front region of the liquid flowing in from the mixing chamber Mi.

EXAMPLE 2

Initial state:

In the waste chamber Abf are present four fleece A CSP 122K (11.2 mm.×12.8 mm., 0.8 mm. thick).

In the fourth pre-chamber V4 is present a fleece B (6 mm.×6 mm., 0.5 mm. thick) coated with 0.15% (w/w) Tween 20.

In the first pre-chamber V1 is present a fleece B (4 mm.×4 mm., 0.5 mm. thick), coated as in Example 1.

In the measurement chamber Me is present a fleece C (8 mm.×12 mm., 0.6 mm. thick), coated as in Example 1.

In the second and third pre-chambers is present, in each case, a fleece B (5 mm.×10 mm., 0.5 mm. thick), coated like the fleece in the second pre-chamber of Example 1.

1st step

In the position illustrated in FIG. 3 (arrow I pointing downwardly), 15 μl. LH-containing serum are introduced into the application chamber A1. The device is then so rotated that the arrow II points downwardly. The serum thereby rinses the reagents present on the fleece T2 into the fleece T1 in the measurement chamber Me. The fleece T1 can completely take up the inflowing amount of liquid. Subsequently, the device is returned to the position illustrated in FIG. 3 (arrow III pointing downwardly).

2nd step

The application chamber A2 is filled with 400 μl. 0.9% sodium chloride solution. This solution is distributed in the regions A2a and A2b of the application chamber A2. At the same time, on fleece T1 there takes place the formation of a sandwich complex of MAB2, analyte and conjugate and the binding thereof to the insoluble reagent via MAB 2.

3rd step

The device is rotated in such a manner that the arrow IV points downwardly. The diluent from the region A2a of the application chamber A2 elutes the fleece T3 and T4 and passes into the mixing chamber Mi.

4th step

After the expiry of the incubation reaction on the fleece T1 (10 minutes), the device is turned via and beyond the initial position illustrated in FIG. 3 so that the arrow V points downwardly. The diluent from the region A2b of the application chamber A2 elutes the fleece T5 and flows through the fleece T1 and T2 into the waste chamber Abf, whereby it takes along the non-fixed reagents on fleece T2 and T1. At the same time, there takes place a substantial homogenisation of the liquid in the mixing chamber Mi. If necessary, the homogenisation can be improved by tilting several times.

5th step

The rotation described in the 4th step is continued at most until the arrow VI points downwardly, thus the openings F1 and F2 lie below. However, it must not be turned too far; the flowing already takes place previously, especially during the rotating. The result is that the diluent flows gradually with the indicator reagents from the mixing chamber Mi through the capillary K4 and the one-way valve E1 into the measurement chamber Me and the desired detection reaction takes place on the fleece T1.

6th step

The reaction on the fleece T1 is measured in the above-described manner.

The filling and tilting of the device can take place according to a predetermined programme in a filling and tilting device.

If fleece contained in the described chamber and already moist are again to be flowed through, this is made easier by placing synthetic resin meshes below the fleece. The use of hydrophobic fleece (teflonised fleece) can also be advantageous for this purpose or the incorporation of ventilation aids, which are advantageously constructed as lattice structures, in the bottoms of the chamber. The influence of the angle of tilt on the speed of flow in the capillaries can be modified by braking fleece.

The homogenisation of the liquid in the mixing chamber can also take place by means of ultrasonics or gas evolution (for example carbon dioxide), in which case the device does not need to be tilted for this purpose.

Figure 4:
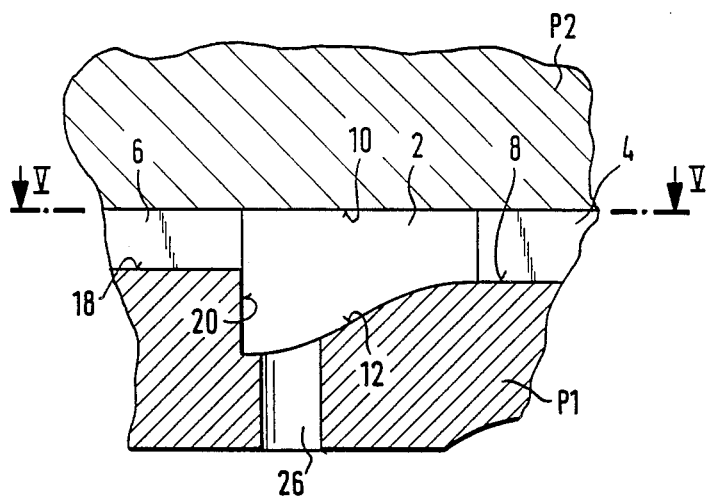
FIG. 4 is a longitudinal section of a static capillary stream one-way valve along the line IV-IV in FIG. 5.
Figure 5:
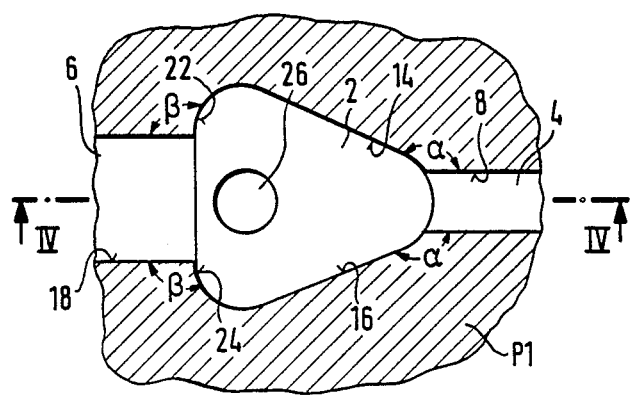
FIG. 5 is a view of the one-way valve along the line V-V in FIG. 4.

A preferred static capillary flow one-way valve, which can be used as one-way valve E1, E2, E3, E4, has, according to FIGS. 4 and 5, a chamber 2 into which opens an inflow capillary 4 and an outflow capillary 6. The wall surfaces 8 of the inflow capillary 4 form, with the bounding wall surfaces 10, 12, 14 and 16 of the chamber 2, angles $\alpha$ which, on average, are greater than the average values of the angles $\beta$ which the wall surfaces 18 of the flow-off capillary 6 form with the bounding wall surfaces 20, 22, 24 of the chamber 2. The apices of the angles $\alpha$ are preferably rounded.

In the embodiment, the in-flow capillary 4 opens into the apex region of the acute-angled widening-out side surfaces 14 and 16 of the chamber 2 and the flow-off capillary 6 at right-angles in a side surface 20, 22, 24 of the chamber lying opposite the apex region in line with the inflow capillary 4. The chamber 2 has a bottom surface 12 into which opens the ventilation canal 26.

Liquid flowing through the inflow capillary 4 is not prevented by the surface tension of its front from entering into the chamber 2, which is further assisted by the ventilation canal 26, and then also enters into the flow-off capillary 6. If liquid attempts to enter from the flow-off capillary 6 into the chamber 2, then it is prevented from doing so by the abrupt transition of the flow-off capillary 6 to the side surfaces 20, 22, 24 as a result of its surface tension.

We claim:

1. Device for determining a component of a sample liquid, said device comprising:
   a measurement chamber containing a first capillary action carrier and a first reagent, which is non-soluble in said sample liquid, adhering to said first capillary action carrier,
   a first pre-chamber containing a second capillary action carrier and a second reagent, which is soluble in said sample liquid, adhering to said second carrier, said second carrier being in bodily capillary contact with said first carrier, said first pre-chamber lying above said measurement chamber in a first working position of said device, a first application chamber having a first filling opening for introduction of said sample liquid and which, in said first working position of said device, lies above said first pre-chamber, a first capillary means connecting said first application chamber to said first pre-chamber, a waste chamber which lies below said measurement chamber in a second working position of said device, gravitational capillary means between said measurement chamber and said waste chamber and permitting flow of liquid from said measurement chamber to said waste chamber only under a predetermined gravitational force, and a second application chamber having a second filling opening for introduction of liquid, said second application chamber being connected via a second capillary means with a second pre-chamber, said second pre-chamber containing at least one indicator reagent on a third capillary action carrier, said second pre-chamber being connected via a third capillary means with a mixing chamber, said mixing chamber being connected via a fourth capillary means with said measurement chamber.

2. Device according to claim 1, wherein said mixing chamber comprises a nose projection.

3. Device according to claim 2 wherein said second capillary means starts from a point of said second application chamber which lies at about the middle of the distance between said second filling opening and the bottom of said chamber lying opposite said second filling opening.

4. Device according to claim 1 wherein said capillary means have hydraulic diameters of 0.04 to 2 mm.

5. Device according to claim 1, wherein said capillary means have hydraulic diameters of 0.2 to 0.6 mm.

6. Device according to claim 1 wherein said capillary action carriers consist of a material selected from the group consisting of paper, fleece, fabric, woven textile and porous membrane material.

7. Device according to claim 1 wherein at least one of said waste chamber and said mixing chamber comprises at least one ventilation opening.

8. Device according to claim 1 further comprising a fourth pre-chamber containing a capillary action carrier which connects said second application chamber with said first pre-chamber.

9. Device according to claim 8, wherein said capillary action carrier consist of a material selected from the group consisting of paper, fleece, fabric, woven textile and porous membrane material.

10. Device according to claim 1, further comprising a first plate with a surface into which said device is incorporated, said first plate being covered by a second plate, wherein at least one of said plate is transparent at least in the region of said measurement chamber.

11. Device of claim 10 wherein said plates comprise a material selected from the group consisting of glass and synthetic resin.

12. Device of claim 11, wherein said synthetic resin is polyacrylate or polystyrene.

13. Device according to claim 1, wherein said second capillary means connects with said second pre-chamber via a static, capillary flow one way valve, said valve permitting flow only into said second pre-chamber.

14. Device according to claim 13, further comprising a first plate with a surface into which said device is incorporated, said first plate being covered by a second plate, wherein at least one of said plate is transparent at least in the region of said measurement chamber.

15. Device of claim 14 wherein said plates comprise a material selected from the group consisting of glass and synthetic resin.

16. Device of claim 15, wherein said synthetic resin is polyacrylate or polystyrene.

17. Device according to claim 1, wherein said fourth capillary means connects with said measurement chamber via a static, capillary flow one-way valve, said valve permitting flow only into said measurement chamber.

18. Device according to claim 17, further comprising a first plate with a surface into which said device is incorporated, said first plate being covered by a second plate, wherein at least one said plate is transparent at least in the region of said measurement chamber.

19. Device of claim 18 wherein said plates comprise a material selected from the group consisting of glass and synthetic resin.

20. Device of claim 19, wherein said synthetic resin is polyacrylate or polystyrene.

21. Device according to claim 1 further comprising a third pre-chamber which lies in series with said second pre-chamber which third pre-chamber contains at least one adjuvant reagent on a fourth capillary action carrier.

22. Device according to claim 21, wherein said capillary action carriers consist of a material selected from the group consisting of paper, fleece, fabric, woven textile and porous membrane material.

23. Device according to claim 21, further comprising a first plate with a surface into which said device is incorporated, said first plate being covered by a second plate, wherein at least one of said plate is transparent at least in the region of said measurement chamber.

24. Device of claim 23 wherein said plates comprise a material selected from the group consisting of glass and synthetic resin.

25. Device of claim 24, wherein said synthetic resin is polyacrylate or polystyrene.

26. Device of claim 1, further comprising a fifth capillary means connecting said second application chamber with said measurement chamber.

27. Device according to claim 26 wherein said fifth capillary means connects to said second application chamber at a height about equal to the height of the filling opening of said second application chamber.

28. Device according to claim 26, wherein a separating wall divides said second application chamber into two regions, a first of which connects with said second capillary means and said second filling opening, and a second of which connects with said fifth capillary means, said wall being less than complete, whereby said regions can be in fluid communication.

29. Device according to claim 26, wherein said capillary means have hydraulic diameters of 0.04 to 2 mm.

30. Device according to claim 26, wherein said capillary means have hydraulic diameters of 0.2 to 0.6 mm.

31. Device according to claim 26, further comprising a first plate with a surface into which said device is incorporated, said first plate being covered by a second plate, wherein at least one of said plates is transparent at least in the region of said measurement chamber.

32. Device of claim 31 wherein said plates comprise a material selected from the group consisting of glass and synthetic resin.

33. Device of claim 32, wherein said synthetic resin is polyacrylate or polystyrene.

34. Device according to claim 1, wherein said fifth capillary means connects with said measurement chamber via a static, capillary flow one-way valve, said valve permitting flow only into said measurement chamber.

35. Device according to claim 34, further comprising a first plate with a surface into which said device is incorporated, said first plate being covered by a second plate, wherein at least one of said plate is transparent at least in the region of said measurement chamber.

36. Device of claim 35 wherein said plates comprise a material selected from the group consisting of glass and synthetic resin.

37. Device of claim 36, wherein said synthetic resin is polyacrylate or polystyrene.

38. Device for determining a component of a sample liquid, said device comprising:
 a measurement chamber containing a first capillary action carrier and a first reagent, which is non-soluble in said sample liquid, adhering to said first capillary action carrier,
 a first pre-chamber containing a second capillary action carrier and a second reagent, which is soluble in said sample liquid, adhering to said second carrier, said second carrier being in bodily capillary contact with said first carrier, said first pre-chamber lying above said measurement chamber in a first working of said device,
 a first application chamber having a first filling opening for introduction of said sample liquid and which, in said first working position of said device, lies above said first pre-chamber,
 a first capillary means connecting said first application chamber to said first pre-chamber,
 a waste chamber which lies below said measurement chamber in a second working position of said device, and
 gravitational capillary means between said measurement chamber and said waste chamber and permitting flow of liquid from said measurement chamber to said waste chamber only under a predetermined gravitational force,
 wherein said second working position is different from said first working position, said gravitational capillary means directly connecting said first pre-chamber with said waste chamber, whereby in said second working position, said liquid flows from said measurement chamber through said first capillary means and said gravitational capillary means.

39. Device according to claim 38, wherein said waste chamber comprises at least one ventilation opening.

40. Device according to claim 38, wherein said capillary means have hydraulic diameters of 0.04 to 2 mm.

41. Device according to claim 38 wherein said capillary means have hydraulic diameters of 0.2 to 0.6 mm.

42. Device according to claim 38, wherein said capillary action carriers consist of a material selected from the group consisting of paper, fleece, fabric, woven textile and porous membrane material.

43. Device according to claim 38 wherein said measurement chamber, first pre-chamber, first application chamber, waste chamber, and said gravitational capillary means are incorporated into a surface of a first plate which is covered by a second plate, wherein at least one of said plates is transparent at least in the region of said measurement chamber.

44. Device according to claim 43, wherein said plates comprise a material selected from the group consisting of glass and synthetic resin.

45. Device according to claim 44, wherein said synthetic resin is polyacrylate or polystyrene.

46. Device according to claim 38, wherein said first capillary means connects with said pre-chamber via a static, capillary flow one-way valve, said valve permitting flow only into said first pre-chamber.

47. Device according to claim 46, further comprising a first plate with a surface into which said device is incorporated, said first plate being covered by a second plate, wherein at least one of said plate is transparent at least in the region of said measurement chamber.

48. Device of claim 47 wherein said plates comprise a material selected from the group consisting of glass and synthetic resin.

49. Device of claim 48, wherein said synthetic resin is polyacrylate or polystyrene.

* * * * *

UNITED STATES PATENT AND TRADEMARK OFFICE
CERTIFICATE OF CORRECTION

PATENT NO.  : 4,985,204
DATED       : January 15, 1991
INVENTOR(S) : Sigmar Klose et al.

It is certified that error appears in the above-identified patent and that said Letters Patent is hereby corrected as shown below:

Column 1, line 5, before the first line, insert --BACKGROUND OF THE INVENTION--.

Column 2, lines 51 and 53, delete "capillary and 53 active".

Column 2, line 58, after "connected by" insert --gravitationl capillary means in the form of--.

Column 3, line 6, delete "capillary-active" and insert --capillary-action--.

Column 5, line 2, delete "sucked up" and insert --absorbed--.

Column 11, (claim 34), change "according to claim 1" to --according to claim 26--.

Column 12, line 18 (new claim 43), after "chamber," insert --said first capillary means--.

Signed and Sealed this

Sixth Day of July, 1993

Attest:

MICHAEL K. KIRK

Attesting Officer

Acting Commissioner of Patents and Trademarks